United States Patent [19]

Kogan et al.

[11] Patent Number: 5,384,331

[45] Date of Patent: Jan. 24, 1995

[54] KETAMINE ANALOGUES FOR TREATMENT OF THROMBOCYTOPENIA

[75] Inventors: Timothy P. Kogan, Half Moon Bay; Todd C. Somers, Montara, both of Calif.

[73] Assignee: Genentech, Inc., San Francisco, Calif.

[21] Appl. No.: 69,245

[22] Filed: May 28, 1993

Related U.S. Application Data

[62] Division of Ser. No. 732,365, Jul. 18, 1991, Pat. No. 5,250,732.

[51] Int. Cl.$^6$ ............... A61K 31/135; C07C 233/06
[52] U.S. Cl. ............... 514/646; 514/647; 514/648; 564/221; 564/192; 564/194; 564/219; 548/304.1; 558/262; 568/329
[58] Field of Search ............... 514/402, 634, 647, 648, 514/646

[56] References Cited

U.S. PATENT DOCUMENTS

| | | | |
|---|---|---|---|
| 2,864,844 | 12/1958 | Davisson | 260/433 |
| 3,254,124 | 5/1966 | Stevens | 260/570.5 |
| 5,032,396 | 7/1991 | Williams | 424/85.2 |
| 5,250,732 | 10/1993 | Kogan et al. | 564/221 |

FOREIGN PATENT DOCUMENTS

| | | |
|---|---|---|
| 0254313A2 | 1/1988 | European Pat. Off. . |
| 0361077 | 4/1990 | European Pat. Off. . |
| 90/09194 | 8/1990 | WIPO . |
| 90/12108 | 10/1990 | WIPO . |
| 91/07988 | 6/1991 | WIPO . |

OTHER PUBLICATIONS

Adams, et al., "Studies on the Biotransformation of Ketamine" *Biomedical Mass Spectrometry* 8(11)527–539 (1981).

Domino, et al., "Phencyclidine and Related Arylcyclohexdylamines: Present and Future Applications" Geneste, eds., NPP Books, Ann Arbor Mich., 1983 pp. 397–409.

Leung, et al., "Comparative Pharmacology in the Rat of Ketamine and its Two Principal Metabolites, Norketamine and (z)–6–Hydroxynorketamine" *J. Med. Chem.* 29:2396–2399 (1986).

Lohmann, et al., "Idiopathic Thrombocytopenia Treated With Paf-Acether Antagonist WEB 2086" *Lancet* p. 1147 (Nov. 1988).

Mason, et al., "Toxicology and Carcinogenesis of Various Chemicals Used in the Preparation of Vaccines" *Clin. Toxicology* 4(2):185–204 (Jun. 1971).

Ogura, et al., "Functional and Morphological Differentiation Induction of a Human Megakaryoblastic Leukemia Cell Line (MEG–01s) by Phorbol Diesters" *Blood* 72(1):49–60 (Jul. 1988).

Parcell, et al., "Synthesis of Ketamine Metabolites I and II and Some Anomalous Reactions of 6–Bromoketamine" *J. Organic Chemistry* 46(25):5055–5060 (Dec. 1981).

Sato, et al., "Establishment of a human leukaemic cell line (CMK) with megakaryocytic characteristics from a Down's syndrome patient with acute megakaryoblastic leukaemia" *British J. of Heaematology* 72:194–190 (1989).

Woolf et al., "Biotransformation of ketamine, (Z)–6–hydroxyketamine, and (e)–6–hydroxyketamine by rat, rabbit, and human liver microsomal preparations" *Xenobiotica* 17(7):839–847 (1987).

*Primary Examiner*—Marianne M. Cintins
*Assistant Examiner*—T. J. Criares
*Attorney, Agent, or Firm*—Daryl B. Winter

[57] ABSTRACT

5,6-Dehydronorketamine and derivatives retaining the $\alpha,\beta$-unsaturated carbonyl are disclosed. These end other Michael or Michael-type acceptors and adducts are shown to influence the replication, differentiation or maturation of blood cells, especially platelet progenitor cells. Accordingly, these compounds are used for treatment of thrombocytopenia.

4 Claims, No Drawings

KETAMINE ANALOGUES FOR TREATMENT OF THROMBOCYTOPENIA

This is a divisional of co-pending application Ser. No. 07/1732,365 filed on Jul. 18, 1991 now U.S. Pat. No. 5,250,732.

FIELD OF THE INVENTION

This application relates to Michael substrates or acceptors, especially certain ketamine analogues. In particular, it relates to compounds that influence the replication, differentiation or maturation of blood cells, especially platelet progenitor cells. This application further relates to the use of ketamine analogues and other Michael substrates to treat thrombocytopenia.

BACKGROUND OF THE INVENTION

I. Megakaryocytopolesis

In the bone marrow pluripotent stem cells differentiate into megakaryocytic, erythrocytic, and myelocytic cell lines. It is believed there is a line of committed cells between stem cells and megakaryocytes. The earliest recognizable member of the megakaryocyte (meg) family are the megakaryoblasts. These cells are initially 20 to 30 μm in diameter having basophilic cyloplasm and a slightly irregular nucleus with loose, somewhat reticular chromatin and several nucleoli. Later, megakaryoblasts may contain up to 32 nuclei, but the cytoplasm remains sparse and immature. As maturation proceeds, the nucleus becomes more lobulate and pyknotic, the cytoplasm increases in quantity and becomes more acidophilic and granular. The most mature cells of this family may give the appearance of releasing platelets at their periphery. Normally, less than 10% of megakaryocytes are in the blast stage and more than 50% are mature. Arbitrary morphologic classifications commonly applied to the megakaryocyte series: are megakaryoblast for the earliest form; promegakaryocyle or basophilic megakaryocyte for the intermediate form; and mature (acidophilic, granular, or platelet-producing) megakaryocyte for the late forms. The mature megakaryocyte extends filaments of cytoplasm into sinusoidal spaces where they detach and fragment into individual platelets (Williams et al., *Hematology*, 1972).

Megakaryocytopoiesis is believed to involve several regulatory factors (Williams et al., *Br. J. Haematol.*, 52:173 [1982] and Williams et al., *J. Cell Physiol.* 110:101 [1982]). The early level of megakaryocytopoiesis is postulated as being mitotic, concerned with cell proliferation and colony initiation from CFU-meg but is not affected by platelet count (Burstein et al., *J. Cell Physiol.* 109:333 [1981] and Kimura et al., *Exp. Hematol.* 13:1048 [1985]). The later stage of maturation is non-mitotic, involved with nuclear polyploidization and cytoplasmic maturation and is probably regulated in a feedback mechanism by peripheral platelet number (Odell et al., *Blood* 48:765 [1976] and Ebbe et al., *Blood* 32:787 [1968]). The existence of a distinct and specific megakaryocyte colony-stimulating factor (meg-CSF) is still in dispute (Mazur, E., *Exp. Hematol.* 15:340–350 [1987]). Although meg-CSF's have been partly purified from experimentally produced thrombocytopenia (Hill et al., *Exp. Hematol.* 14:752 [1986]) and human embryonic kidney conditioned medium [CM] (McDonald et al., *J. Lab. Clin. Med.* 85:59 [1975]) and in man from aplastic anemia and idiopathic thrombocylopenic purpura urinary extracts (Kawakita et al., *Blood* 6:556 [1983]) and plasma (Hoffman et al., *J. Clin. Invest.* 75:1174 [1985]), their physiological function is as yet unknown in most cases. The conditioned medium of pokeweed mitogen-activated spleen cells (PWM-SpCM) and the murine myelomonocyte cell line WEHI-3 (WEHI-3CM) have been used as megakaryocyte potentiators. PWM-SpCM contains factors enhancing CFU-meg growth (Metcalf et al., *Pro. Natl. Acad. Sci., USA* 72:1744–1748 [1975]; Quesenberry et al., *Blood* 65:214 [1985]; and Iscove, N. N., in *Hematopoietic Cell Differentiation*, ICN-UCLA Symposia on Molecular and Cellular Biology, Vol. 10, Golde et al., eds. [New York, Academy Press] pp 37–52 [1978]), one of which is interleukin-3 (IL-3), a multilineage colony stimulating factor (multi-CSF [Burstein, S. A., *Blood Cells* 11:469 [1986]). The other factors in this medium have not yet been identified and isolated. WEHI-3 is a mudne myelomonocytic cell line secreting: relatively large amounts of IL-3 and smaller amounts of GM-CSF. IL-3 has been purified and cloned (Ihle et al., *J. Immunol.* 129:2431 [1982]) and has been found to potentlate the growth of a wide range of hemopoietic cells (Ihle et al., *J. Immunol.* 13:282 [1983]). IL-3 has also been found to synergize with many of the known hemopoietic hormones or growth factors (Bartelmez et al., *J. Cell Physiol.* 22:362–369 [1985] and Warren et al., *Cell* 46:667–674 [1988]), including both erythropoietin (EPO) and H-1 (later known as interleukin-1 or IL-1), in the induction of very early multipotential precursors and the formation of very large mixed hemopoietic colonies.

Other sources of megakaryocyte potentiators have been found in the conditioned media of mudne lung, bone, macrophage cell lines, peritoneal exudate cells and human embryonic kidney cells. Despite certain conflicting data (Mazur, E., *Exp. Hematol.* 15:340–350 [1987]), there is some evidence (Geissler et al., *Br. J. Haematol.* 60:233–238 [1985]) that activated T lymphocytes rather than monocytes play an enhancing role in megakaryocytopoiesis. These findings suggest that activated T-lymphocyte secretions such as interleukins may be regulatory factors in meg development (Geissler et al., *Exp. Hernatol.* 15:845–853 [1987]). A number of studies on megakaryocytopoiesis with purified EPO (Vainchenker et al., *Blood* 54:940 [1979]; McLeod et al., *Nature* 261:492–4 [1976]; and Williams et al., *Exp. Hematol.* 12:734 [1984]) indicate that this hormone has an enhancing effect on meg colony formation. More recently this has been demonstrated in both serum-free and serum- containing cultures and in the absence of accessory cells (Williams et al., *Exp. Hematol.* 12:734 [1984]). EPO was postulated to be involved more in the single and two-cell stage aspects of megakaryocytopoiesis as opposed to the effect of PWM-SpCM which was involved in the four-cell stage of megakaryocyte development. The interaction of all these factors on both early and late phases of megakaryocyte development remains to be elucidated.

Other documents of interest include: Eppstein et al., U.S. Pat. No. 4,962,091; Chong, U.S. Pat. No. 4,879,111; Fernandes et al., U.S. Pat. No. 4,604,377; Wissler et al., U.S. Pat. No. 4,512,971; Gottlieb, U.S. Pat. No. 4,468,379; Kimura et al., *Eur. J. Immunol.*, 20(9): 1927–1931 (1990); Secer, W. E. et al., *J. of Immunol.*, 144(4):1484–1489 (1990); Warren, D. J., et al., *J. of Immunol.*, 140(1): 94–99 (1988); Warren, M. K. et al.,,, *Exp. Hematol.*, 17(11): 1095–1099 (1989); Bruno, E., et al.,,, *Exp. Hematol.*, 17(10): 1038–1043 (1989); Tanikawa et al.,, *Exp. Hematol.*, 17(8): 883–888 (1989); Koike et al., *Blood*, 75(12): 2286–2291 (1990); Lotem, et al., *Blood*, 75(5): 1545–1551 (1989); Rennick, D., et al., *Blood*, 73(7): 1828–1835 (1989); and Clutterbuck, E. J., et al., *Blood*, 73(6): 1504–1512 (1989)

II. Thrombocytopenia

Platelets are critical elements of the blood clotting mechanism. Depletion of the circulating level of platelets, called thrombocytopenia, occurs in various clinical conditions and disorders. Thrombocytopenia is defined as a platelet count below $150 \times 10^9$ per liter. The major causes of thrombocytopenia can be broadly divided into three categories on the basis of platelet life span. Thus, thrombocytopenia may be classified as due to (1) impaired production of platelets by the bone marrow, (2) platelet sequestration in the spleen (splenomegaly), or (3) increased destruction of platelets in the peripheral circulation (e.g. autoimmune thrombocytopenia). Additionally, in patients receiving large volumes of rapidly administered platelet-poor blood products, thrombocytopenia may develop due to dilution.

The clinical bleeding manifestations of thrombocylopenia depend on the severity of thrombocytopenia, its cause, and possible associated coagulation defects. In general, patients with platelet counts between 20 and $100 \times 10^9$ per liter are at risk of excessive posttraumatic bleeding, while those with platelet counts below $20 \times 10^9$ per liter may bleed spontaneously. For any given degree of thrombocytopenia, bleeding tends to be more severe when the cause is decreased production rather than increased destruction of platelets; in the latter situation, accelerated platelet turnover results in the circulation of younger, larger and hemostatically more effective platelets. Thrombocytopenia may result from a variety of disorders briefly described below. A more detailed description may be found in Schafner, A. I., Thrombocytopenia and Disorders of Platelet Function, *Internal Medicine*, 3rd Ed., John J. Hutton et al., Eds., Little Brown and Co., Boston/Toronto/London, (1990).

(a) Thrombocylopenia due to impaired platelet production

Causes of congenital thrombocytopenia include constitutional aplastic anemia (Fanconi syndrome) and congenital amegakaryocytic thrombocytopenia, which may be associated with skeletal malformations. Acquired disorders of platelet production are caused by either hypoplasia of megakaryocytes or ineffective thrombopoiesis. Megakaryocytic hypoplasia can result from a variety of conditions, including marrow aplasia (including idiopathic forms or myelosuppression by chemotherapeutic agents or radiation therapy), myelfibrosis, leukemia, and invasion of the bone marrow by metastatic tumor or granulomas. In some situations, toxins, infectious agents, Or drugs may interfere with thrombopoiesis relatively selectively; examples include transient thrombocytopenias caused by alcohol and certain viral infections and mild thrombocytopenia associated with the administration of thiazide diuretics. Finally, ineffective thrombopoiesis secondary to megaloblastic processes (folate or $B_{12}$ deficiency) can also cause thrombocytopenia, usually with coexisting anemia and leukopenia.

Current treatment of thrombocytopenias due to decreased platelet production depends on identification and reversal of the underlying cause of the bone marrow failure. Platelet transfusions are usually reserved for patients with sedous bleeding complications or for coverage during surgical procedures, since isoimmunization may lead to refractodness to further platelet transfusions. Mucosal bleeding resulting from severe thrombocytopenia may be ameliorated by the oral or intravenous administration of the antifibdnolytic agents. Thrombotic complications may develop, however, if antifibrinolytic agents are used in patients with disseminated intravascular coagulation (DIC).

(b) Thrombocytopenia due to splenic sequestration

Splenomegaly due to any cause may be associated with mild to moderate thrombocytopenia. This is a largely passive process (hypersplenism) of splenic platelet sequestration, in contrast to the active destruction of platelets by the spleen in cases of immunomediated thrombocytopenia discussed below. Although the most common cause of hypersplenism is congestive splenomegaly from portal hypertension due to alcoholic cirrhosis, other forms of congestive, infiltrative, or lymphoproliferative splenomegaly are also associated with thrombocytopenia. Platelet counts generally do not fall below $50 \times 10^9$ per liter as a result of hypersplenism alone.

(c) Thrombocytopenia due to nonimmune-mediated platelet destruction

Thrombocytopenia can result from the accelerated destruction of platelets by various nonimmunologic processes. Disorders of this type include disseminated intravascular coagulation, prosthetic intravascular devices, extracorporeal circulation of the blood, and thrombotic microangiopathies such as thrombotic thrombocytic purpura. In all of these situations, circulating platelets that are exposed to either artificial surfaces or abnormal vascular intima either are consumed at these sites or are damaged and then prematurely cleared by the reticuloendothelial system. Disease states or disorders in which disseminated intravascular coagulation (DIC) may arise are set forth in greater detail in Braunwald et al. (eds), *Harrison's Principles of Internal Medicine*, 1 lth Ed., p. 1478, McGraw Hill (1987). Intravascular prosthetic devices, including cardiac valves and intra-aortic balloons can cause a mild to moderate destructive thrombocytopenia and transient thrombocytopenia in patients undergoing cardiopulmonary bypass or hemodialysis may result from consumption or damage of platelets in the extracorporeal circuit.

(d) Drug-induced immune thrombocytopenia

More than 100 drugs have been implicated in immunologically mediated thrombocytopenia. However, only quinidine, quinine, gold, sulfonamides, cephalothin, and heparin have been well characterized. Drug-induced thrombocytopenia is frequently very severe and typically occurs precipitously within days while patients are taking the sensitizing medication.

(e) Immune (autoimmune) thrombocytopenic purpura (ITP)

ITP in adults is a chronic disease characterized by autoimmune platelet destruction. The autoantibody is usually IgG although other immunoglobulins have also been reported. Although the autoantibody of ITP has been found to be associated with platelet membrane GPIibllla, the platelet antigen specificity has not been identified in most cases. Extravascular destruction of sensitized platelets occurs in the reticuloendothelial system of the spleen and liver. Although over one-half of all cases of ITP are idiopathic, many patients have underlying rheumatic or autoimmune diseases (e.g. systemic lupus erythematosus) or lymphoproliferative disorders (e.g. chronic lymphocytic leukemia).

(f) HIV-induced ITP

ITP is an increasingly common complication of HIV infection (Morris et al., *Ann. Intern. Med.*, 96:714–717 [1982]), and can occur at any stage of the disease progression, both in patients diagnosed with the Acquired Immune Deficiency Syndrome (AIDS), those with AIDS-related complex, and those with HIV infection but without AIDS symptoms. HIV infection is a transmissible disease ultimately characterized by a profound deficiency of cellular immune function as well as the occurrence of opportunistic infection and malignancy. The primary immunologic abnormality resulting from infection by HIV is the progressive depletion and functional impairment of T lymphocytes expressing the CD4 cell surface glycoprotein (H. Lane et al., *Ann. Rev. Immunol.*, 3:477 [1985]). The loss of CD4 helper/inducer T cell function probably underlies the profound defects in cellular and humoral immunity leading to the opportunistic infections and malignancies characteristic of AIDS (H. Lane supra).

Although the mechanism of HIV-associated ITP is unknown, it is believed to be different from the mechanism of ITP not associated with HIV infection. (Walsh et al., *N. Eng. J. Med.*, 311:635–639 [1984]; and Ratner, L., *Am. J. Med.*, 86:194–198 [1989]).

III. Therapy

The therapeutic approach to the treatment of patients with HIV-induced ITP is dictated by the severity and urgency of the clinical situation. The treatment is similar for HIV-associated and non-HIV-related ITP, and although a number of different therapeutic approaches have been used, the therapy remains controversial.

Platelet counts in patients diagnosed with ITP have been successfully increased by glucocorticoid (e.g. prednisolone) therapy, however in most patients the response is incomplete, or relapse occurs when the glucocorticoid dose is reduced or its administration is discontinued. Based upon studies with patients having HIV-associated ITP, some investigators have suggested that glucocorticoid therapy may result in predisposition to AIDS. Glucocorticoids are usually administered if platelet count falls below $20 \times 10^9$/liter or when spontaneous bleeding occurs.

For patients refractory to glucocorticoids, the compound 4-(2-chlorphenyl)-9methyl-2-[3-( 4- morpholinyl)- 3-propanon- 1 -yl]6H-thieno[3,2, f][1,2,4]triazolo[4,3,a,][1,4]diazepin (WEB 2086) has been successfully used to treat a severe case of non HIV-associated ITP. A patient having platelet counts of 37,000–58,000/μl was treated with WEB 2086 and after 1-2 weeks treatment platelet counts increased to 140,000–190,000/μl. (EP 0361077A2 and Lohman, H., et al., *Lancet:*1147 [1988]).

Although the optimal treatment for acquired amegacaryocytic thrombocytopenia purpura (AATP) is uncertain, antithymocyte globulin (ATG), a horse antiserum to human thymus tissue, has been shown to produce prolonged complete remission (Trimble, M. S., et al., *Am. J. Hematol*, 37:126–127 [1991]). A recent report however, indicates that the hematopoietic effects of ATG are attributable to thimerosal, where presumably the protein acts as a mercury carrier (Panella, T. J., and Huang, A. T., *Cancer Research:*50:4429–4435 [1990]).

Good results have been reported with splenectomy. Splenectomy removes the major site of platelet destruction and a major source of autoantibody production in many patients. This procedure results in prolonged treatment-free remissions in a large number of patients. However, since surgical procedures are generally to be avoided in immune compromised patients, splenectomy is recommended only in severe cases of HIV-associated ITP. In patients who fail to respond to 2 to 3 weeks of glucocorticoid treatment, or do not achieve sustained response after discontinuation of glucocorticoid administration. Based upon current scientific knowledge, it is unclear whether splenectomy predisposes patients to AIDS.

In addition to prednisolone therapy and splenectomy, certain cytotoxic agents, e.g. vincristine, and azidothimidine (AZT, zidovudine) also show promise in treating HIV-induced ITP however, the results are preliminary.

None of the foregoing methods for treatment of thrombocytopenia suggest using a Michael acceptor, Michael-type acceptor, or reverse or retrograde Michael adduct.

It will be appreciated from the foregoing that one way to treat thrombocytopenia would be to obtain an agent capable of accelerating the differentiation and maturation of megakaryocytes or precursors thereof into the platelet-producing form. Considerable efforts have been expended on identifying such an agent, commonly referred to as "thrombopoeitin" (TPO). Thrombopoeitin activity was observed as early as 1959 (Rak et al., *Med. Exp.*1:125) and attempts to characterize and purify this agent have continued to the present day. While reports of partial purification of thrombopoeitin-active polypeptides exist (see, for example, Tayrien et al., *J. Biol. Chem.* 262:3262 [1987] and Hoffman et al., *J. Clin. Invest.* 75:1174 [1985]), others have postulated that thrombopoeitin is not a discrete entity in its own right but rather is simply the polyfunctional manifestation of a known hormone (IL-3, Sparrow et al., *Prog. Clin. Biol. Res.*, 215:123 [1986]). Regardless of its form or origin, a molecule possessing thrombopoetic activity would be of significant therapeutic value.

Accordingly, it is an object of this invention to obtain a pharmaceutically pure molecule capable of stimulating differentiation and maturation of megakaryocytes into the mature platelet-producing form.

It is another object to provide the molecule in a form for therapeutic use in the treatment of thrombocytopenia.

These and other objects of the invention will be apparent to the ordinary artisan upon consideration of the specification as a whole.

SUMMARY OF THE INVENTION

The objects of the invention are achieved by providing a novel mammalian megakaryocytopoietic maturation promoting compound capable of stimulating maturation and/or differentiation of megakaryocytes into the mature platelet-producing form. The novel compounds are Michael or Michael-type acceptors and adducts. The preferred compounds having this megakaryocytopoietic activity are represented by structural formulae I and II.

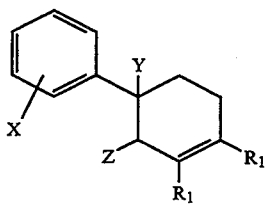

I

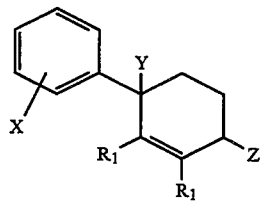

II where:

X is selected from hydrogen, halogen (F, Cl, Br, I), alkyl (R—), and alkoxy (RO—); Y is selected from hydroxy (HO—), —NHR₂ and —NR₂R₃ provided that when the compound is represented by structural formula I, —NHR₂ and —NR₂R₃ am not —NH₂ or —NHCH₃; Z is selected from oxo (O=), alkylenedioxy (—ORO—), hydroxy (HO—), and alkoxy (RO—); each R1 is independently selected from hydrogen and alkyl (R—), R₂ and R₃ are independently selected from biotinoyl and either substituted or unsubstituted alkyl (R—), aryl (Ar—), alkanoyl (R—C(=O)—), and aralkyl (Ar—R—) where the substituents are selected from: halo (F, Cl, Br, I) cyano (NC—), azido (N₃—), nitro (O₂N—), amino (H₂N—), imino (=NH), amidino (H₂NC(=NH)—), aminomethyleneamino (H₂N—CH=N—), iminomethylamino (HN=CH—NH—), guanidino (H₂N—C(=NH)—NH—), N^G-aminoguanidino (H₂N—HN—C(=NH)—NH—), alkylamino (RNH—), dialkylamino (R₂N—), alkylideneamino (R₂C=N—), acylamino (RCOHN—), N,N-diacylamino (ROC(ROC)N—), N-alkyl-N-acylamino (R(ROC)N—), formylamino (HCONH—), formimidoyl (CH(=NH)—), ureido (H2NCONH—), alkylsulfonamido (RSO2NH—), N-alkyl-N-alkylsulfonylamino (RSO2RN—), thioformyl (SHC—), alkylthiocarbonyl (SRC—), thioformamido(SHCNH—), N-alkyl-N-thioformylamino (SHCRN—), thioacylamino (RSCHN—), N-alkyl-N-thioacylamino (SRCRN—), thioureido (H2NCSHN—), alkylsulfinamido (RSORN—), N-alkyl-N-alkylsulfinylamino (RSOHN—), carboxy (HO2C—), carbalkoxy (RCO2—), formyl (OCH—), alkylcarbonyl (ROC—), formyloxy (OCHO—), alkanoyloxy (ROCO—), carbamoyl or carboxamido (H₂NCO—), N-alkylcarboxamido (RNHCO—), N,N-dialkylcarboxamido (R₂NCONH—), carbamoyloxy (H₂NOCO—), N-alkylcarbamoyloxy (RNHOCO—), N,N-dialkylcarbamoyloxy (R₂NOCO—), mercapto or sulfhydryl (SH—), alkylthio (RS—), alkylsulfinyl (RSO—), alkylsulfonyl (RSO₂), alkylsulfonato (ROSO₂—), sulfo (HOSO₂—), sulfonamido (H₂NSO₂—), N-alkylsulfonamido (RNHSO₂—), N,N-dialkylsulfonamido (R₂NSO₂—), hydroxy (HO—), alkyloxy (RO—), alkyl (R—), alkenyl (R=R—), alkynyl (RR—), cycloalkyl (R(—R—)R—), aryl (Ar—), aralkyl (ArR—), and heterocycloalkyl (R(—X'—)-(—R—)—) or heteroaryl (Ar(X')—) having from 1 to 3 dngs, each ring having from 0-3 hetero (X') atoms selected from N, O, and S, provided that at least one ring contains a heteroatom (for example; thienyl, furyl, pyranyl, pyrrolyl, imadazolyl, pyrazolyl, isothiazolyl, isoxazolyl, pyddyl, pyrazinyl, pydmidinyl, pyddazinyl, indolizinyl, isoindolyl, 3H-indolyl, indolyl, 1H-indazolyl, pudnyl, 4H quinolizinyl, isoquinolyl, quinolyl, phthalzinyl, naphyddinyl, quinoxalinyl, quinazolinyl, cinnolinyl, pteridinyl, 4aH-carbazolyl, carbazolyl, β-carbolinyl, phenanthddinyl, acddinyl, pedmidinyl, phenanthrolinyl, phenazinyl, phenarsazinyl, phenothiazinyl, furazanyl, penoxazinyl, isochromanyl, chromanyl, pyrrolinyl, imidazolidinyl, imidazolinyl, pyrazolidinyl, pyrazolinyl, piperidyl, piperazinyl, indolinyl, isoindolinyl, quinuclidinyl, morpholinyl, and the like), where each alkyloxy, alkyl, alkenyl, heterocycloalkyl, heteroaryl, aryl and aralkyl may be optionally substituted with halo (F, Cl, Br, I), amino, alkylamino, carboxy, alkyloxy and hydroxy, and where R is $C_1$-$C_{12}$ alkyl, preferably $C_1$-$C_6$ alkyl and most preferably methyl or ethyl; or R₂ and R₃ taken together may form an alkylene [(—R—) where R is preferably $C_4$-$C_8$, most preferably $C_4$-$C_5$] or an oxydialkylene [(—R—O—R) where the two R's taken together contain from 4 to 8 carbons], and pharmaceutically acceptable salts thereof, The preferred compound of the instant invention is represented by formula

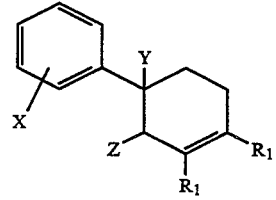

Formula I where R₁ may be either hydrogen or methyl and R₂ and R₃ are independently selected from; hydrogen (provided both R₂ and R₃ are not simultaneously hydrogen), methyl (provided that if either R₂ or R₃ is hydrogen, the other is not methyl), 3-aminophenylmethyl, 3-amino-2-iodaphenylmethyl, biotinoyl, acetyl, phenylethyloxycarbonyl, malonoyl, 3-(methylthio)propanoyl, or 3-(methylsulfinyl)-propanoyl, The more preferred compounds of the instant invention include:

6-acetylamino-6-(2-chlorophenyl)-2 cyclohexen- 1 -one;

6-(2-chlorophenyl)-6-(1-phenylethyloxycarboxyamino)-2-cyclohexen-1-one;

6-(2-aminoacetyl)amino-6-(2-chlorophenyl)-2-cyclohexen-1-one;

6-(2-chiorophenyl)-6-(3-(methylthio )propanoyl )amino-2-cyclohexen-1-one;

6-(2-chlorophenyl)-6-hydroxy-2-cyclohexen-1-one;

6-biotinoylamino-6-(2-chlorophenyl)-2-cyclohexen-1-one;

6-(2-chlorophenyl)-6-(3-(aminophenyl)methyl)amino-2-cyclohexen-1-one;

6-(2-chlorophenyl)-6-methylamino-2-cyclohexen-1-one;

6-(2-chlorophenyl)-6-phenyimethlamino-2-cyclohexen-1-one;

6-(2-chlorophenyl)-6-(3-(methylsulfinyl)propanoyl-)amino-2-cyclohexen-1-one; and 6-(2-chlorophenyl)-6-(3-(methylsulfonyl)propanoyl-)amino-2-cyclohexen-1-one, while the most preferred compounds are the stereoisomers of the foregoing compounds substantially free from its corresponding enantiomer or diastereomer.

The invention includes a method for treating a mammal having thrombocytopenia comprising administering a therapeutically effective amount of a Michael or Michael-type acceptor, or a Michael or Michael-type adduct to the mammal. Preferably the Michael or Michael-type acceptor is the compound of formulae I or II as defined above, and includes 5,6-dehydronorketamine, 5,6-dehydroketamine.

Optionally, the Michael or Michael-type acceptor may be administered in combination with a cytokine, especially a colony stimulating factor or interleukin, specifically with; G-CSF, CSF-1, GM-CSF, M-CSF, erythropoietin, IL-1, IL-3, IL-4, IL-5, IL-6, IL-7, or IL-8.

When the method for treating thrombocytopenia comprises administering a Michael or Michael-type adduct, preferably the donor will be selected from; G-CSIF, CSF-1, GM-CSF, M-CSF, erylhropoietin, IL-1, IL-3, IL-4, IL-5, IL-6, IL-7, or IL-8 and preferably the acceptor will be a compound represented by formulae I or II, especially 5,6-dehydronorketamine and 5,6-dehydroketamine.

DETAILED DESCRIPTION OF THE INVENTION

I. Definitions

In general, the following words or phrases have the indicated definition when used in the description, examples, and claims.

Cytokine is a generic term for proteins released by one cell population which act on another cell as intercellular mediators. Examples of such cytokines are lymphokines, monokines, and traditional polypeptide hormones. Included among the cytokines are growth hormone, insulin-like growth factors, human growth hormone, N-methionyl human growth hormone, bovine growth hormone, parathyroid hormone, thyroxine, insulin, proinsulin, relaxin, prorelaxin, glycoprotein hormones such as follicle stimulating hormone (FSH), thyroid stimulating hormone (TSH), and leutinizing hormone (LH), hemopoietic growth factor, hepatic growth factor, fibroblast growth factor, prolactin, placental lactogen, tumor necrosis factor-alpha and -beta, mulled-aninhibiting substance, mouse gonadotropin-associated peptide, inhibin, activin, vascular endothelial growth factor, integrin, thrombopoietin, nerve growth factors such as NGF-$\beta$, platelet-growth factor, transforming growth factors (TGFs) such as TGF-alpha and TGF-beta, insulin-like growth factor-I and -II, erythropoietin, osteoinductive factors, interferons such as interferon-alpha, -beta, and -gamma, colony stimulating factors (CSFs) such as macrophage-CSF (M-CSF), granulocyte-macrophage-CSF (GM-CSF), and granulocyte-CSF (G-CSF), intedeukins (ILs) such as IL-1, IL-2, IL-3, IL-4, IL-5, IL-6, IL-7, IL-8 and other polypeptide factors. As used herein the foregoing terms are ment to include proteins from natural sources or from recombinant cell culture. Similarly, the terms are intended to include biologically active equivalents; e.g. differing in amino acid sequence by one or more amino acids or in type or extent of glycosylation.

Michael condensations or reactions are defined as nucleophillic addition reactions between electron rich donors of the type HY (where typically Y is of the form $Z-C^--R_2$, i.e. a nucleophillic carbanion where R may be alkyl, aryl, H, or another Z [Z as defined below]) and electrophillic acceptors, specifically the most electron poor carbon of an unsaturated carbon-carbon bond conjugated to an electron withdrawing group, of the type C=C-Z (where Z is the electron withdrawing group and is typically of the form; CHO, COR [including quinones], COOR, CONH, CN [including quinone imides], $NO_2$, SOR, $SO_2R$, $SR_2$, and the like [R as defined above]). It will be understood that the unsaturated carbon-carbon bond may be either a double or triple bond and may be further conjugated to one or more additional double or triple bonds, or additional electron withdrawing groups Z. It will also be understood that the condensation will be, initially at least, a 1,4- ("conjugate") addition or occasionally a 1,2- addition, or when the acceptor is further conjugated, a 1,6- or higher addition.

Michael-type condensations or reactions are defined as extensions of the above reaction to condensations involving non-carbanion nucleopiles, including sulfur and nitrogen, that react by the same mechanism, i.e. 1,4-addition, with Michael acceptors.

The product of a Michael or Michael-type condensation is referred to as a Michael or Michael-type adduct.

Michael or Michael-type acceptors or substrates are compounds containing unsaturated carbon-carbon bonds conjugated to electron withdrawing groups as described above. Typically, they will contain $\alpha,\beta$-ethylenic carbonyl groups or the equivalent including; $\alpha,\beta$-ethylenic aldehydes (eg. acrolein. crotonaldehyde, or cinnamaldehyde), aliphatic $\alpha,\beta$-ethylenic ketones, $\alpha,\beta$-acetylenic ketones, aromatic $\alpha,\beta$-ethylenic ketones, heterocyclic $\alpha,\beta$-ethylenic ketones, cycloalkenones, acyl cycloalkenes, $p$-qunones, $\alpha,\beta$-unsaturated nitdies, $\alpha,\beta$-unsaturated amides, unsaturated imides (eg. N-ethylmaleimide), $\alpha,\beta$-ethylenic aliphatic esters, alicyclic $\alpha, \beta$-ethylenic esters, aromatic $\alpha,\beta$-ethylenic esters, aromatic $\alpha,\beta$-acetylenic esters, $\alpha,\beta$-ethylenic nitro compounds, $\alpha,\beta$-ethylenic sulfoxides and sulfones, $\alpha,\beta$-ethylenic phosphonates, 2- and 4- vinylpyridines, fulvenes, and cyclopropane derivatives (eg. ethyl 1-cyanocyclopropane-1-carboxylate).

Michael or Michael-type donors are generally Lewis bases where the electron donor pair is located on a carbon ($R_3C:-$), sulfur (RS:−), or nitrogen ($R_2N:-$). Typically, the donor will be a mercaptan, amine, or carbonyl compound of the form $O=C-CHR_2$, having an acidic $\alpha$ hydrogen.

A reverse or retrograde Michael or Michael-type reaction is the opposite of the condensation reaction in which the adduct splits apart into the precursor donor and acceptor reactants. This process is refered to as a retrogression reaction.

Stereoisomers are defined as compounds that have the same molecular formula but differ from each other only in the way the atoms are oriented in space.

Thrombocytopenia is defined as a platelet count below $150 \times 10^9$ per liter of blood.

Thrombopoeitic activity is defined as biological activity that consists of accelerating the differentiation and/or maturation of megakaryocytes or megakaryocyte precursors into the platelet producing form of these cells. This activity may be measured in various assays including an in-vivo mouse platelet rebound synthesis assay, induction of platelet cell surface antigen assay as measured by an anti-platelet immunoassay (anti-GPI$_b$III$_a$) for a human leukaemia megakaryoblastic cell line (CMK), and induction of polyploidization in a megakaryoblastic cell line(DAMI).

Thrombopoeitin (TPO) is defined as a compound having Thrombopoeitic activity or being capable of increasing serum platelet counts in a mammal. TPO is preferrably, capable of increasing endogenous platelet counts by at least 10%, more preferably by 50%, and most preferrably capable of elevating platelet counts in a human to greater that $150 \times 10^9$ per liter of blood.

II. Preferred Embodiments of the Invention

The novel mammalian megakaryocyte maturation promoting compounds represented by structural formulae I and II above are produced from ketamine or norketamine by standard procedures known in the art.

By ketamine and norketamine is meant those compounds represented by structural formulae III and IV.

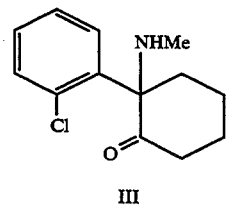 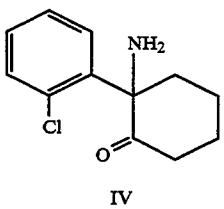

III    IV

Ketamine and norketamine are also known as 2-(2-chlorophenyl)-2-(methylamino) cyclohexanone and 2-(amino)-2-(2-chlorophenyl) cyclohexanone respectively. Ketamine and norketamine may be prepared by the procedures set forth in U.S. Pat. No. 3,254,124. Ketamine is also available commercially.

Ketamine is a nonbarbituate anesthetic having a rapid acting general anesthetic action producing a profound anesthetic state characterized by normal pharyngeal-laryngeal reflexes, normal or slightly enhanced skeletal muscle tone, cardiovascular and respiratory stimulation and transient respiratory depression. Ketamine has also been described as useful in treating and preventing stroke (EP 0254,313). Neither of these activities or effects suggest that ketamine, norketamine or analogues thereof would possess megakaryocyte maturation promoting activity.

In fact, neither ketamine nor norketamine possess thrombopoeitic activity in various assays (at concentrations as high as 200 μM). Surprisingly however, a ketamine catabolite, 5,6-dehydronorketamine (V), was found to be active at concentrations of 15 μM and 30 μM in the CMK and DAMI assays (described below) respectively.

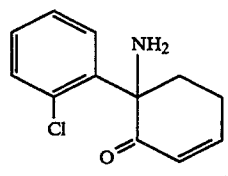

V
5,6-dehydronorketamine
(active @ 15 μM [CMK] and 30 μM [DAMI])

Thrombopoeitic activity may be measured in various assays including an in-vivo mouse platelet rebound synthesis assay, induction of platelet cell surface antigen assay as measured by an anti-platelet immunoassay (anti-GPII$_b$III$_a$) for a human leukaemia megakaryoblastic cell line (CMK)(see Sato, T., et al., Brit. J. Heamatol. 72:184–190 (1989)),and induction of polyploidization in a megakaryoblastic cell line(DAMI)(see Ogura, M., et Al., Blood 72(1):49–60 (1988). Maturation of megakaryocyles from immature, largely non-DNA synthesizing cells, to morphologically identifiable megakaryocytes involves a process that includes appearance of cytoplasmic organelles, acquisition of membrane antigens (GPII$_b$III$_a$), endoreplication and release of platelets as described in the background. A lineage specific promoter (i.e. TPO) of megakaryocyte maturation, would be expected to induce these changes in immature megakaryocytes leading to platelet release and alleviation of thympocylopenia. Thus, assays were designed to measure the emergence of these parameters in immature megakaryocyte cell lines, i.e. CMK and DAMI cells. The CMK assay (Example VIII) measures the appearance of a specific platelet marker, GPII$_b$III$_a$, and platelet shedding. The DAMI assay (Example IX) measures endoreplication since increases in ploidy are hallmarks of mature megakaryocytes. Recognizable megakaryocytes have ploidy values of 2N, 4N, 8N, 16N, 32N, etc. Finally, the in vivo assay (Example X) demonstrates that administration of the test compound results in elevation of platelet numbers.

It was the surprising discovery that a known catabolite (Parcell, R., et al., J. Org. Chem., 46(25): 5055–5060 [1981]) of ketamine possessed megakaryocyte maturation activity in each of these assays (see Table 1 ) that lead to the present invention.

5,6,-dehydronorketamine can be conveniently prepared according to scheme I.

SCHEME I

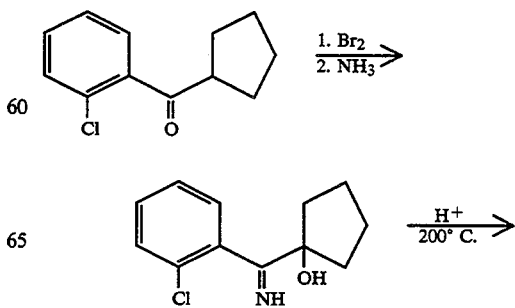

-continued
SCHEME I

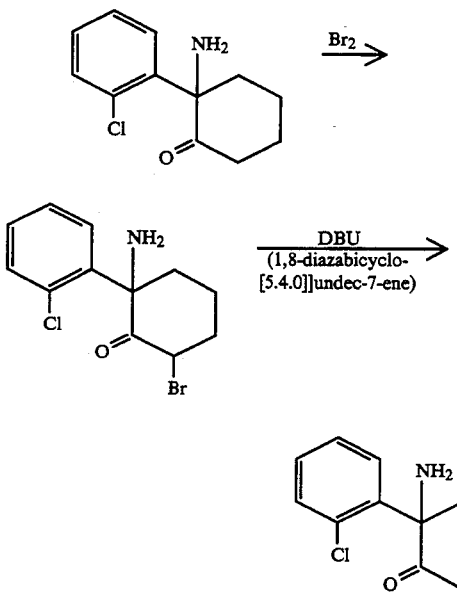

It was initially thought that maintaining the basic character of the amine group was essential for retention of the novel thrombopoeitic activity observed. However, N-acylation of 5,6-dehydronorketamine produced an even more active derivative, N-acetyl-5,6-dehydronoketamine (VI).

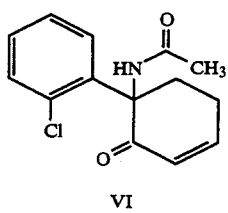
VI

It is now believed, without intending to be limited to any particular theory or mechanism, that the active compounds exert their activity by parcipitating in vivo in a Michael, or Michael-type addition (see e.g. March, J., Advanced Organic Chemistry, $3^{rd}$ ed. [John Wiley and ,Sons: New York, [1985]]665; Bergman, E. et al., Organic Reactions, 10:179-555[1959]; House, H., Modern Synthetic Reactions, 595-623 [W. A. Benjamin, Menlo Park, Calif. $2^{nd}$ ed., 1972]; and Stork, G., et al., J. Am. Chain. Soc. 104:310 [1982]) and thus the $\alpha$, $\beta$ unsaturation adjacent to the oxo (ketone) or equivalent group is believed to be Important to the activity of these compounds. Accordingly, one of ordinary skill will appreciate that the instant claimed compounds are of the type: >C=C—Z, where Z is typically an aldehyde, ketone or a carboxylic acid derivative, end that numerous analogues capable of Michael addition would produce equivalent results (see tables I–XXII in Bergman, et el., supra). Thus, for example, it is believed that other substituents Z, such as; CHO, COR, COOR, $CONH_2$, CN, $NO_2$, SOR, $SO_2R$, and the like would demonstrate TPO activity as well. Similarly, increasing the extent of conjugation, as for example with compounds of the type: >C=C—C=C—Z, or conjugated triple bonds would produce compounds capable of 1, 2, 1, 4, or 1, 6 Michael addition. Furthermore, masked Michael acceptors (Michael adducts) of the type: RXC-CHR-Z, where X is a leaving group such as OR, SR, NR2, or halogen, would an similarly through an addition-elimination type mechanism. Therefore, one of ordinary skill will appreciate that numerous analogues of 5,6,-dehydronorkmamine or the equivalent can be prepared involving, for example; N-acylation, carbonyl reduction, ketal formation, diezotization and replacement of the amine, formation of sulfonamides, aromatic ring substitution, and the like, according to exemplary Schemes II and III.

SCHEME II

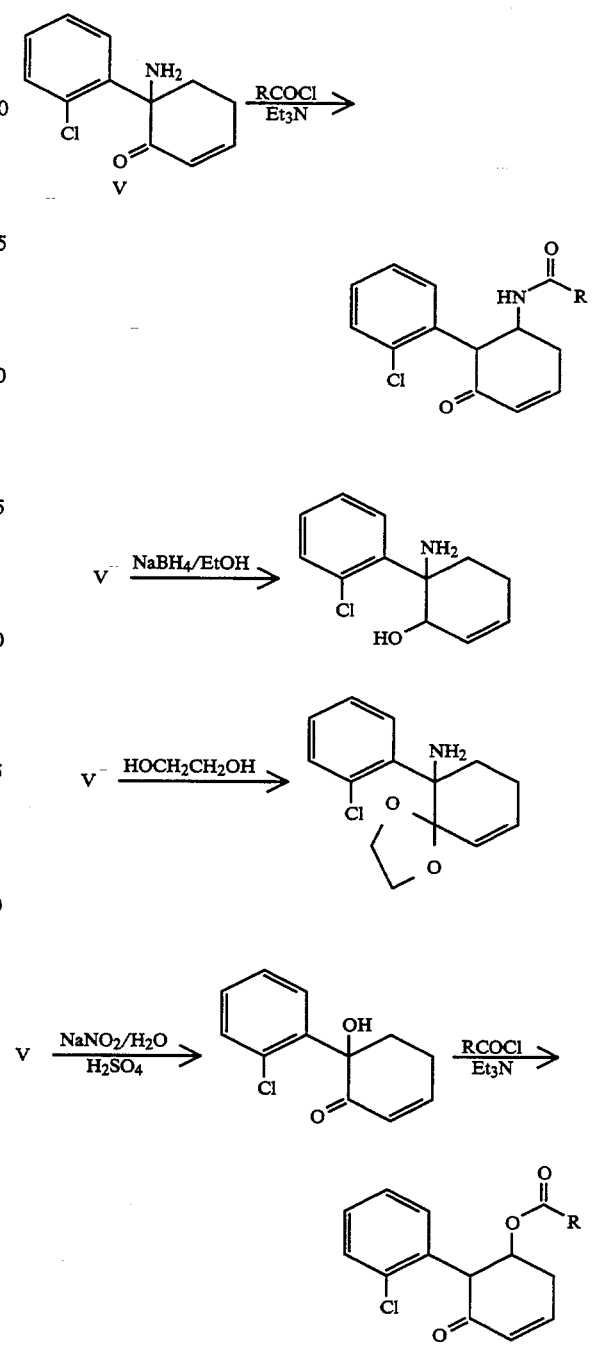

-continued
SCHEME II

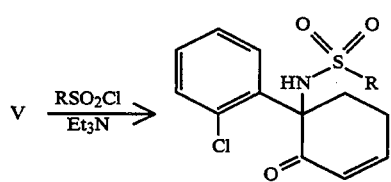

SCHEME III

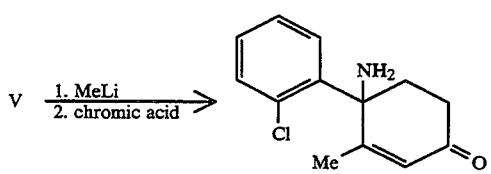

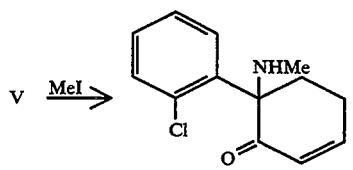

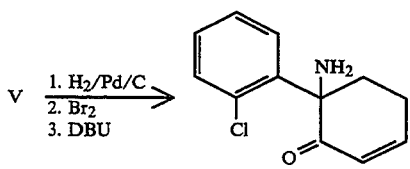

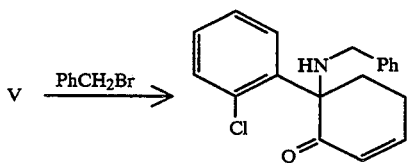

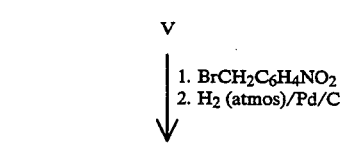

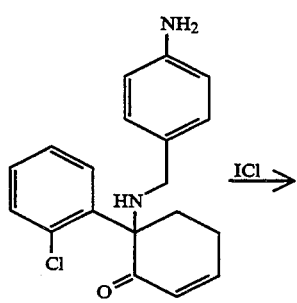

-continued
SCHEME III

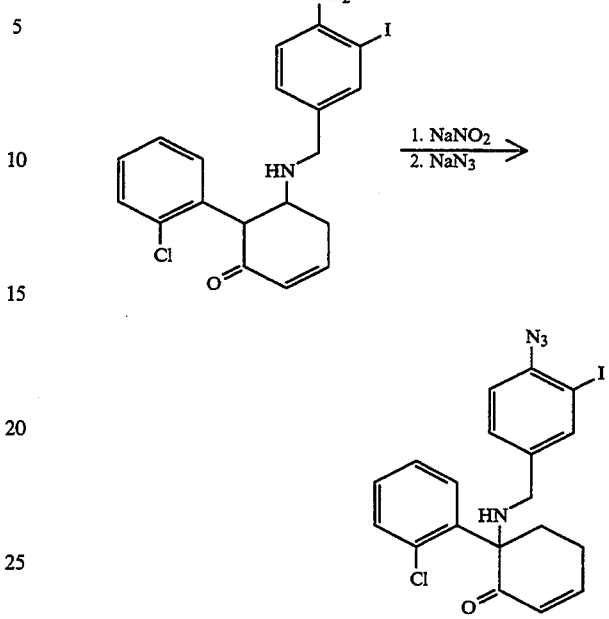

Other compounds having the important α,β unsaturation represented by structural formulae I and II can be prepared, purified and resolved by analogous procedures known in the art.

The most preferred compounds are those having the greatest thrombopoietic activity. For example, compounds having DAMI assay values of less than 100 μM are suitable. Preferred compounds have values less than 501μM and most preferred have values of 15 μM or lower. Exemplary preferred compounds include:

6-acetylamino-6-(2-chlorophenyl)-2cyclohexen-1-one;

6-(2-chlorophenyl)-6-(1-phenylethyioxy carboxyamino)-2-cyclohexen-1-one;

6-(2-aminoacetyl)amino-6-(2-chlorophenyl)-2-cyclohexen-1-one;

6-(2-chlorophenyl)-6-(3-(methylthio )propanoyl-)amino-2-cyclohexen-1-one;

6-(2-chlorophenyl)-6-hydroxy-2-cyclohexen-1-one;

6-biotinoylamino-6-(2-chlorophenyl)-2-cyclohexen-1-one;

6-(2-chlorophenyl)-6-(3-(aminophenyl)methyl-)amino-2-cyclohexen-1-one;

6-(2-chlorophenyl)-6-methylamino-2-cyclohexen-1-one;

6-(2-chlorophenyl)-6-phenylmethlamino-2-cyclohexen-1-one;

6-(2-chlorophenyl)-6-(3-(methylsulfinyl)propanoyl-)amino-2-cyclohexen-1-one; and 6-(2-chlorophenyl)-6-(3-(methylsulfonyl)propanoyl-)amino-2-cyclohexen-1-one.

These compounds are all substantially more active in the DAMI assay than the prior art compound WEB 2086 (EP 0361077A2), which was inactive at a concentration of 200 μM.

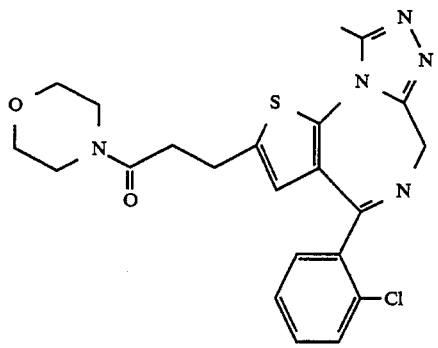

-continued
(<200 μM)
WEB 2086

Table 1 sets forth thrombopoetic activity, as measured by the DAMI and CMK assays, of synthetically or otherwise related compounds to those of the instant invention.

TABLE 1

| | Thrombopoietic activity | | |
|---|---|---|---|
| COMPOUND | CMK (μM) | DAMI (μM) | In vivo (% ctl. @ mg/mouse/d) |
| ketamine (III) | inactive @ 200 | inactive @ 200 | |
| IV | inactive @ 200 | inactive @ 200 | |
| V | 6 | 25 | 131 @ 2 |
| (+)-V | 6 | 12 | |
| (−)-V | 6 | 12 | |
| VI | 6 | 12 | |
| VII | 12 | 25 | |
| WEB 2086 | inactive @ 200 | inactive @ 200 | |
| thimerosal | 0.75 | 1.5 | |
| cyclohexenone | 200 | 200 | |
| 1,4-naphthoquinone | <6 | inactive @ 200 | |
| 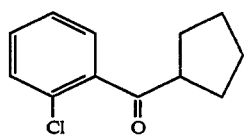 | inactive @ 200 | inactive @ 200 | |
| 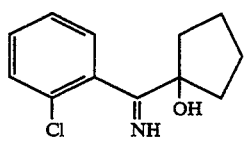 | inactive @ 200 | inactive @ 200 | |
| 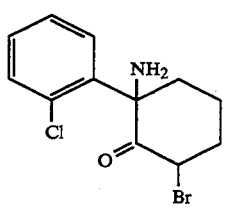 | inactive @ 200 | inactive @ 200 | |
| 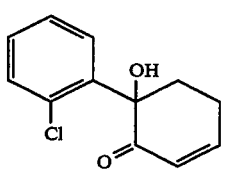 | 6 | 25 | |
| 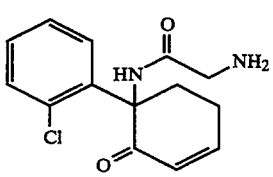 | 12 | 50 | |

TABLE 1-continued

| | Thrombopoietic activity | | |
|---|---|---|---|
| COMPOUND | CMK (μM) | DAMI (μM) | In vivo (% ctl. @ mg/mouse/d) |
| (structure) | 6 | 10 | |

In addition to the therapeutic utility, the ketamine analogue compounds of the instant invention are believed to be useful for labelling and isolating a putative receptor for the postulated thrombopoietin. For example, the biotinolated dehydronorketamine compound (VII) may be useful to isolate a putative TPO receptor. Briefly, cells believed to contain the TPO receptor are homogenized in a suitable buffer, preferably one containing a nonionic or other detergent that will solubilize membrane proteins without denaturing the receptor. An appropriate amount of compound VII may be admixed with the tissue hominate containing the putative receptor under conditions favoring formation of a Michael of Michael-type adduct. The resuting mixture is contacted with avidin immobilized on an insoluble matrix and eluted with a buffer to separate unreacted membrane proteins from the biotinylated receptor (see e.g. Swack. J., et al., Anal Blochem. 87:114–126 (1978). The receptor may then be recovered from the column under conditions favoring retrograde Michael or Michael-type condensation.

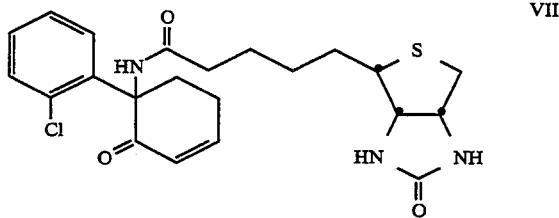
VII

III. Therapeutic Use of the Ketamine Analogues 5,6-dehydroketamine, 5,6-dehyronorketamine, and compounds of formulae I and III may be used in a sterile pharmaceutical preparation or formulation to stimulate thrombopoeitic activity in patients suffering from thrombocytopenia due to impaired production, sequestration, or increased destruction of platelets. Thombocylopenias associated bone marrow hypoplasia (e.g., aplastic anemia following chemotherapy or bone marrow transplant) may be effectively treated with the compounds of this invention as well as disorders such as disseminated intravascular coagulation (DIC), immune thrombocytopenia (including HIV-induced ITP and non HIV-induced ITP) and thrombotic thrombocytopenia. Additionally, these compounds may be useful in treating mycloproliferative thrombocytotic diseases as well as thrombocylosis from inflammatory conditions and in iron deficiency.

Still other disorders usefully treated with the compounds of this invention include defects or damage to platelets resulting from poisoning or activation on artificial surfaces. In these cases, the instant compounds may be employed to stimulate "shedding" of new "undamaged" platelets. For a more complete list of useful applications, see the "Background" supra, especially section (a)–(f) and references cited therein.

The compounds of the instant invention may be employed alone or in combination with other cylokines, hematopoietins, interleukins, growth factors, or antibodies in the treatment of the above-identified disorders and conditions. Thus, the instant compounds may be employed in combination with other protein or peptide having thrombopoeitic activity including; G-CSF, CSF-1, GM-CSF, M-CSF, IL-1, IL-3, IL-4, IL-5, erythropoietin (EPO), IL-6, IL-7, and IL-8.

The compounds of the instant invention are prepared in a mixture with a pharmaceutically acceptable carder. This therapeutic composition can be administered orally, intravenously or through the nose or lung. The composition may also be administered parenterally or subcutaneously as desired. When administered systemically, the therapeutic composition should be pyrogen-free and in a parenterally acceptable solution having due regard for pH, isotonicity, and stability. These conditions are known to those skilled in the art. Briefly, dosage formulations of the compounds of the present invention are prepared for storage or administration by mixing the compound having the desired degree of purity with physiologically acceptable carriers, excipients, or stabilizers. Such materials are non-toxic to the recipients at the dosages and concentrations employed, and include buffers such as phosphate, citrate, acetate and other organic acid salts; antioxidants such as ascorbic acid; low molecular weight (less than about ten residues) peptides such as polyarginine, proteins, such as serum albumin, gelatin, or immunoglobulins; hydrophilic polymers such as polyvinylpyrrolidinone; amino acids such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sobitol; counterions such as sodium and/or nonionic surfactants such as Tween, Pluronics or polyethyleneglycol.

About 0.5 to 500 mg of a compound or mixture of compounds of formula I, and II as the free acid or base form or as a pharmaceutically acceptable salt, is compounded with a physiologically acceptable vehicle, carrier, excipient, binder, preservative, stabilizer, flavor, etc., as called for by accepted pharmaceutical practice. The amount of active ingredient in these compositions is such that a suitable dosage in the range indicated is obtained.

Typical adjuvants which may be incorporated into tablets, capsules and the like are a binder such as acacia, corn starch or gelatin; an excipient such as microcrystalline cellulose; a disintegrating agent like corn starch or alginic acid; a lubricant such as magnesium stearate;

a sweetening agent such as sucrose or lactose; a flavoring agent such as peppermint, wintergreen or cherry. When the dosage form is a capsule, in addition to the above materials it may also contain a liquid carrier such as a fatty oil. Other materials of various types may be used as coatings or as modifiers of the physical form of the dosage unit. A syrup or elixer may contain the active compound, a sweetener such as sucrose, preservatives like propyl paraben, a coloring agent and a flavoring agent such as cherry. Sterile compositions for injection can be formulated according to conventional pharmaceutical practice. For example, dissolution or suspension of the active compound in a vehicle such as water or naturally occurring vegetable oil like sesame, peanut, or cottonseed oil or a synthetic fatty vehicle like ethyl oleste or the like may be desired. Buffers, preservatives, antioxidants and the like can be incorporated according to accepted pharmaceutical practice.

The dosage will be determined by the attending physician taking into consideration various factors known to modify the action of drugs including severity and type of disease, body weight, sex, diet, time and route of administration, other medications and other relevant clinical factors. Typically, the daily regimen will range from 1-3000 μg/kg body weight. Preferably the dosage will range from 10-1000 μg/kg body weight. Most preferably, the dosage will range from 50 to 150 mg/day. Therapeutically effective dosages may be determined by either in vitro or in vivo methods.

IV. Therapeutic Use of Michael Acceptors and Adducts

In addition to ketamine analogues, other Michael or Michael-type acceptors or substrates have similarly been found to have thrombopoietic activity in assays described herein. Thus it is believed that a therapeutically effective amount of a Michael acceptor or Michael adduct capable of retrogression may be used to treat thrombocytopenia. Michael adducts that do not undergo retrogression readily are believed to be ineffective in treating thrombocytopenia because the concentration of free Michael acceptor produced in the retrogression reaction is too low to form an adduct with the in vivo donor. It is believed, for example, that an adduct formed between a donor protein and an acceptor like N-ethylmaleimide would not be a preferred Michael adduct for treatment of thrombocylopenia. Conversely, an adduct formed between a protein such as G-CSF, CSF-1, GM-CSF, IL-1, IL-3, IL-4, IL-5, erythropoietin (EPO), IL-6, IL-7, IL-8, or M-CSF and an acceptor like 5,6,-dehydronorketamine would be a preferred adduct.

EXAMPLES

Without further description, it is believed that one of ordinary skill in the art can, using the preceding description and illustrative examples, make and utilize the present invention to the fullest extent. The following working examples therefore specifically point out preferred embodiments of the present invention, and are not to be construed as limiting in any way of the remainder of the disclosure.

EXAMPLE I

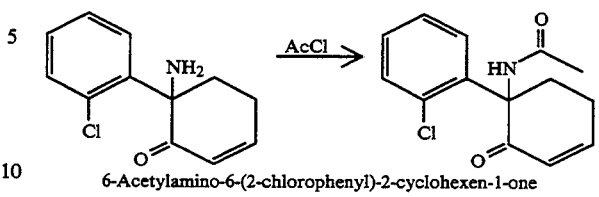

6-Acetylamino-6-(2-chlorophenyl)-2-cyclohexen-1-one

Acetyl chloride (142 μl, 1.8 mmol) was added to a solution of 6-amino-6-(2-chlorophenyl)-2-cyclohexen-1-one (R. F. Parceli and J. P. Sanchez, *J. Org. Chem.*, 46:5055 [1981]), (200 mg, 0.9 mmol) and triethylamine (1.0 ml) in dichloromethane (10 ml), and the reaction stirred at room temperature for 1 h. Analysis by TLC indicated complete reaction, and the mixture was partitioned between ethyl acetate and 1N HCl. The organic phase was washed with brine, dried ($MgSO_4$), and the solvent removed by evaporation. Flash chromatography on silica gel eluted with 1:1 ethyl acetate/hexane afforded 6-acetylamino-6-(2-chlorophenyl)-2-cyclohexen-1-one which crystallized on standing, m.p. 144°-145° C.

EXAMPLE II

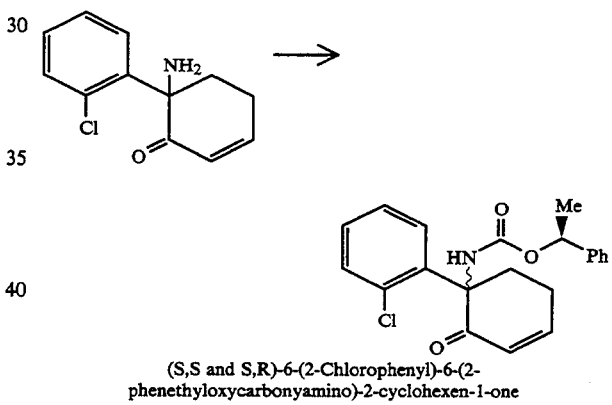

(S,S and S,R)-6-(2-Chlorophenyl)-6-(2-phenethyloxycarbonyamino)-2-cyclohexen-1-one (S)-sec-Phenethylchloroformate was prepared by adding 2,6-lutidine (954 μl, 8.2 mmol) in hexane (10 ml) to a stirred solution of phosgene (6.4 ml of 20% soln. In toluene, 12.3 mmol) and (S)-(−)-sec,-phenethyl alcohol (1.0 g, 8.2 mmol) at 0° C. The reaction was monitored by TLC to insure completion, and was worked up by partitioning between hexane and 1N HCl. The organic phase was washed with brine, dried ($MgSO_4$), and the solvent removed by evaporation, and the residue redissolved in dichloromethane (2 ml). Dropwise addition of a solution of 6-amino-6-(2-chlorophenyl)-2-cyclohexen-1-one (100 mg, 0.45 mmol) and 2,6-lutidine (52 μl, 0.45 mmol) in dichloromethane (3 ml) to the chloroformate, and stirring for 3 h gave the crude carbamates. The reaction was partitioned between ethyl acetate and 1N HCl. The organic phase was washed with water, brine, dried ($Na_2SO_4$), and the solvent removed by evaporation. Separation of the diastereoisomers was achieved by chromatography on a silica HPLC column eluted with 1:5 ethyl acetate/hexane, which gave (S,S and S,R)-6-(2-chlorophenyl)-6-(2-phenethyloxycarbonyamino)-2-cyclohexen-1-one (80 mg first isomer, and 70 mg second isomer, 90% overall yield).

EXAMPLE III

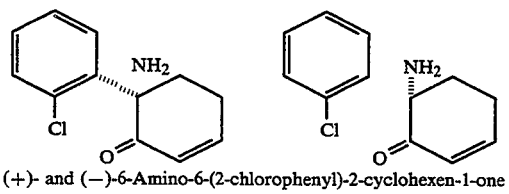

(+)- and (−)-6-Amino-6-(2-chlorophenyl)-2-cyclohexen-1-one

Each separated diastereoisomer of (S,S and S,R)-6-(2-chlorophenyl)-6-(2-phenethyloxycarbony-amino)-2-cyclohexen-1-one (80 mg, 0.22 mmol, and 70 mg, 0.19 mmol) were dissolved in methanol (5 ml), concentrated HCl (2 ml) added and the reactions mixed and stood at room temperature for 4 h, at which point TLC indicated complete reaction. Each reaction was made basic with 10% sodium hydroxide and extracted with ethyl acetate (2x). The organic phases were washed with saturated bicarbonate, brine, dried ($Na_2SO_4$), and the solvent removed by evaporation. Flash chromatography on silica gel eluted with 1:1 ethyl acetate/hexane afforded (−)-6-amino-6-(2-chlorophenyl)-2-cyclohexen-1-one from the less polar carbamate (24.9 mg, 51%), $[\alpha]D^{20} = -48.1°$ (c=1.245, MeOH), and (+)-6-amino-6-(2-chlorophenyl)-2-cyclohexen-1-one from the more polar carbamate (29.2 mg, 69%). $[\alpha]D^{20} = +40.7°$ (c=1.46, MeOH). Both compounds were found to be active at 6 μm in either a CMK or DAMI assay. 5,6-DNK is an abbreviation derived from the common or trivial name of the compound 5,6-dehdronorketamine.

EXAMPLE IV

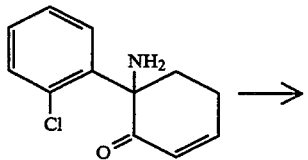

6-(2-Aminoacetyl)amino-6-(2-chlorophenyl)-2-cyclohexen-1-one

A solution of 6-amino-6-(2-chlorophenyl)-2-cyclohexen-1-one (50 mg, 0.23 mmol), N-(tert-butoxycarbonyl)glycine (47 mg, 0.27 mmol), hydroxybenzotriazole (31 mg, 0.23 mmol), and 1-(3-dimethylaminopropyl)-3-ethylcarbodiimide hydrochloride (66 mg, 0.35 mmol) in dimethylformamide (1 ml) was stirred at room temperature for 18 h. The reaction was partitioned between saturated bicarbonate and ethyl acetate, the organic phase was washed with brine, dried ($Na_2SO_4$), and the solvent removed by evaporation. The residue was dissolved in dichloromethane (2 ml), trifluoroacetic acid (2 ml) was added and stirred at room temperature for 1 h, followed by evaporation of the solvent and a normal work up. Purification was achieved by preparative thin layer chromatography on silica gel eluting with ethyl acetate. Isolation of the UV and ninhydrin positive band at Rf 0.2 gave 6-(2-aminoacetyl)amino-6-(2-chlorophenyl)-2-cyclohexen-1-one (28 mg, 43%). The title compound was found to be active at 6μm in both the CMK and DAMI assay.

EXAMPLE V

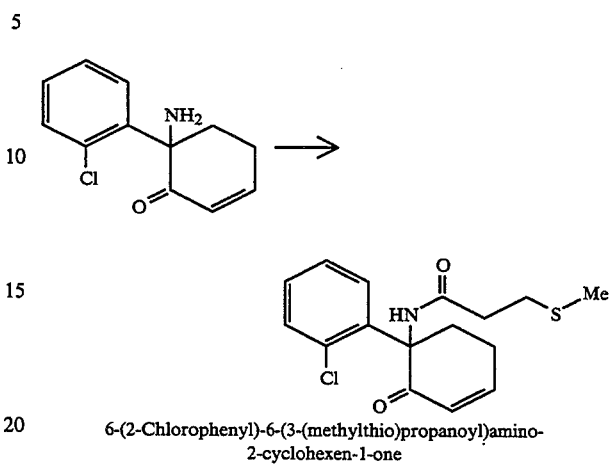

6-(2-Chlorophenyl)-6-(3-(methylthio)propanoyl)amino-2-cyclohexen-1-one

A solution of 6-amino-6-(2-chlorophenyl)-2-cyclohexen-1-one (50 mg, 0.23 mmol), 3(methylthio)propanoic acid (prepared by the known base hydrolysis from the commercial methyl ester)(33 mg, 0.28 mmol), hydroxybenzotriazole (31 mg, 0.23 mmol), and 1-(3-dimethylaminopropyl)-3-ethylcarbodiimide hydrochloride (66 mg, 0.35 mmol) in dimethylformamide (1 ml) was stirred at room temperature for 18 h. The reaction was partitioned between saturated bicarbonate and ethyl acetate, the organic phase was washed with brine, dried ($Na_2SO_4$), and the solvent removed by evaporation. Purification was achieved by preparative thin layer chromatography on silica gel eluting with 1:1 ethyl acetate/hexane. Isolation of the UV active band at Rf 0.4 gave 6-(2-chlorophenyl)-6-(3-(methylthio)-propanoyl)amino-2-cyclohexen- 1-one (60.6 mg, 65%). The title compound was found to be active at 6μm in the CMK assay.

EXAMPLE VI

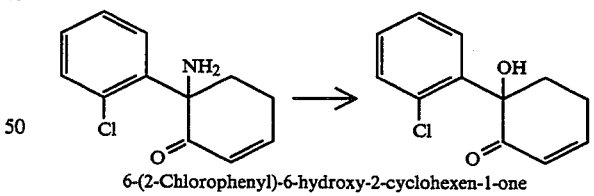

6-(2-Chlorophenyl)-6-hydroxy-2-cyclohexen-1-one

Sodium nitrite (16 mg, 0.23 mmol) in water (0.5 ml) was added to a stirred solution of 6-amino-6-(2-chlorophenyl)-2-cyclohexen-1-one (50 mg, 0.23 mmol)in 1/3 N HCI (1.5 ml) at 0° C. After 1 h the reaction was neutralized with sodium hydroxide and allowed to warm to room temperature for 30 minutes. The reaction was partitioned between saturated bicarbonate and ethyl acetate, the organic phase was washed with brine, dried ($Na_2SO_4$), and the solvent removed by evaporation. Purification was achieved by preparative thin layer chromatography on silica gel eluting with 3:2 ethyl acetate/hexane. Isolation of the UV active band at Rf 0.7 gave 6-(2-Chlorophenyl)-6-(2-cyclohexen-1-one (14.2 mg, 28%).

EXAMPLE VII

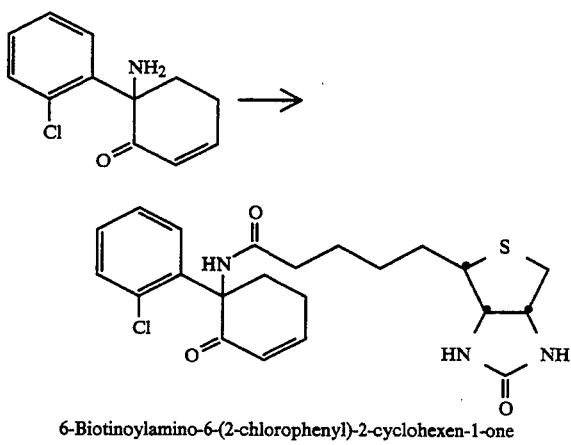

6-Biotinoylamino-6-(2-chlorophenyl)-2-cyclohexen-1-one

A solution of 6-amino-6-(2-chlorophenyl)-2-cyclohexen-1-one (50 mg, 0.23 mmol), (+)-biotin (56 mg, 0.23 mmol), hydroxybenzotdazole (31 mg, 0.23 mmol), and 1-(3-dimethylaminopropyl)-3-ethylcarbodiimide hydrochloride (66 mg, 0.35 mmol) in dimethylformamide (1 ml) was stirred at room temperature for 42 h. The reaction was partitioned between water and ethyl acetate, the organic phase was washed with water, brine, dried ($Na_2SO_4$), and the solvent removed by evaporation. Flash chromatography on silica gel eluted with 17:3 ethyl acetate / hexane afforded 6-biotinoylamino-6-(2-chlorophenyl)-2-cyclohexen-1-one (32.7 mg, 32%).

EXAMPLE VIII

CMK assay for thrombopoletin (TPO) induction of platelet antigen $GPII_bIII_a$ expression CMK cells are maintained in RMPI 1640 medium (Sigma) supplemented with 10% fetal bovine serum and 10 mM glutamine. In preparation for the assay, the cells are harvested, washed and resuspended at $5 \times 10^5$ cells/ml in serum-free GIF medium supplemented with 5 mg/L bovine insulin, 10 mg/L apo-transferrin, 1×trace elements. In a 96-well flat-bottom plate, the TPO standard or experimental samples are added to each well at appropriate dilutions in 100 µl volumes. 100 µl of the CMK cell suspension is added to each well and the plates are incubated at 37° C., in a 5% $CO_2$ incubator for 48 hours. After incubation, the plates are spun at 1000 rpm at 4° C. for five minutes. Supernatants are discarded and 100µl of the FITC-conjugated GPII-$bIII_1$ monoclonal 2D2 antibody is added to each well. Following incubation at 4° C. for 1 hour, plates are spun again at 1000 rpm for five minutes. The supernatants containing unbound antibody are discarded and 200 µl of 0.1% BSA-PBS wash is added to each well. The 0.1% BSA-PBS wash step is repeated three times. Cells are then analyzed on a FASCAN using standard one parameter analysis measuring relative fluorescence intensity.

EXAMPLE IX

DAMI assay for thrombopoletin (TPO) by measuring endomitotic activity of DAMi cells on 96-well microtiter plates DAMI cells are maintained in IMDM+10% horse serum (Gibco) supplemented with 10 mM glutamine, 100 ng/ml Penicillin G, and 50 µg/ml streptomycin. In preparation for the assay, the cells are harvested, washed, and resuspended at $1 \times 10^6$ cells/ml in IMDM+1% horse serum. In a 96-well round-bottom plate, 100 µl of the TPO standard or experimental samples is added to DAMI cell suspension. Cells are then incubated for 48 hours at 37° in a 5% $CO_2$ incubator. After incubation, plates are spun in a Sorvall 6000B centrifuge at 1000 rpm for five minutes at 4° C. Supernatants are discarded and 200 µl of PBS-0.1% BSA wash step is repeated. Cells are fixed by the addition of 200 µl ice-cold 70% Ethanol-PBS and resuspended by aspiration. After incubation at 4° C. for 15 minutes, the plates are spun at 2000 rpm for five minutes and 150 µl of 1 mg/ml RNAse containing 0.1 mg/ml Propidium Iodide and 0.05% Tween-20 is added to each well. Following a one hour incubation at 37° C. the changes in DNA content are measured by flow cytometry. Polyploidy is measured and quantitated as follows:

Normalized Polyploid Ratio (NPR) =

$$\frac{(\% \text{ Cells in } >G2 + M/\% \text{ Cells in } <G2 + M) \text{ with TPO}}{(\% \text{ Cells in } >G2 + M/\% \text{ Cells in } <G2 + M) \text{ in control}}$$

EXAMPLE X

Thrombopoletin (TPO)in vivo assay (Mouse Platelet Rebound Assay)

In vivo Assay for $^{35}S$ Determination of Platelet Production

C57BL6 mice (obtained from Charles River) were injected intraperitoneally (IP) with 1 ml goat anti-mouse platelet serum (6 amps) on day 1 to produce thrombocytopenia. On days 5 and 6, mice were given two IP injections of the factor or PBS as the control. On day 7, thirty µCi of $Na_2^{35}SO_4$ in 0.1 ml saline were injected intravenously and the percent $^{35}S$ incorporation of the injected dose into circulating platelets was measured in blood samples obtained from treated and control mice. Platelet counts and leukocyte counts were made at the same time from blood obtained from the retro-orbital sinus.

While the invention has necessarily been described in conjunction with preferred embodiments and specific working examples, one of ordinary skill, after reading the foregoing specification, will be able to effect various changes, substitutions of equivalents, and alterations to the subject matter set forth herein, without departing from the spidt and scope thereof. Hence, the invention can be practiced in ways other than those specifically described herein. It is therefore intended that the protection granted by Letters Patent hereon be limited only by the appended claims and equivalents thereof.

All references cited herein are hereby expressly incorporated by reference.

We claim:

1. A method for treating a mammal for thrombocytopenia comprising administering to a mammal in need of such treatment a therapeutically effective amount of a composition comprising a compound represented by the following structural formulae I or II

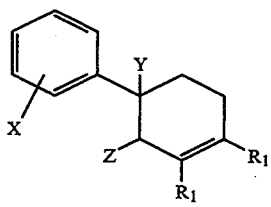

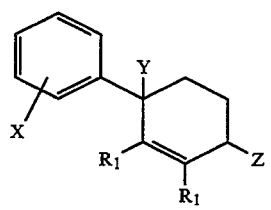

where:
X is selected from one or more of the group
hydrogen;
halogen;
$C_1$–$C_6$ alkyl; and
$C_1$–$C_6$ alkoxy;
Y is selected from the group
hydroxy;
—$NHR_2$; and
—$NR_2R_3$;
Z is selected from the group;
oxo;
$C_2$–$C_4$ alkylenedioxy;
hydroxy; and
$C_1$–$C_6$ alkoxy;
$R_1$, each occurrence, is independently selected from the group;
hydrogen; and
$C_1$–$C_6$ alkyl;
$R_2$ and $R_3$ are independently selected from the group:
unsubstituted or substituted $C_1$–$C_6$ alkyl;
unsubstituted or substituted $C_6$–$C_{14}$ aryl;
unsubstituted or substituted $C_1$–$C_6$ alkanoyl;
unsubstituted or substituted $C_7$–$C_9$ aralkyl; and
biotinoyl;
wherein the substitutents are selected from one or more of the group halo; cyano; azido; nitro; amino; amidino; imino; aminomethyleneamino; iminomethylamino; guanidino; $N^G$-aminoguanidino; $C_1$–$C_6$-alkylamino; $C_2$–$C_{10}$-dialkylamino; $C_2$–$C_{10}$alkylideneamino; $C_2$–$C_6$-acylamino; formylamino; N-($C_1$–$C_6$)alkyl-N-($C_1$–$C_6$-)acylamino; $C_1$–$C_6$alkylsulfonamido; N-($C_1$–$C_6$)alkyl-N-($C_1$–$C_6$)-alkylsulfonylamino; thioformamido; N-($C_1$–$C_6$)alkyl-N-thioformylamino; thio($C_1$–$C_6$-)acylamino; N-($C_1$–$C_6$)alkyl-N-thio($C_1$–$C_6$)acylamino; thioureido; $C_2$–$C_6$-alkylsulfinamido; N-($C_1$–$C_6$)alkyl-N-($C_1$–$C_6$)alkylsulfinylamino; N,N-di($C_1$–$C10$)acylamino; carboxy; $C_2$–$C_6$ carbalkoxy; formyl; $C_2$–$C_6$ alkylcarbonyl; formyloxy; $C_2$–$C_6$ alkanoyloxy; carbamoyl (carboxamido); N-($C_1$–$C_6$)alkylcarboxamido; N,N-di($C_1$–$C_{10}$)alkylcarboxamido; carbamoyloxy; N-($C_1$–$C_6$) carbamoyloxy; N, N-di($C_1$–$C_6$)alkylcarbamoyloxy; mercapto; $C_1$–$C_6$ alkylsulfinyl; $C_1$–$C_6$ alkylsulfonyl; $C_1$–$C_6$ alkylsulfonato; $C_1$–$C_6$ alkylthio; sulfonamido; N-($C_1$–$C_6$)alkylsulfonamido; N,N-di($C_1$–$C_6$)alkylsulfonamido; hydroxy; $C_1$–$C_6$ alkyloxy; $C_1$–$C_6$ alkyl optionally substituted with halo amino, $C_1$–$C_6$ alkylamino, carboxy, $C_1$–$C_4$ alkoxy, and hydroxy; $C_2$–$C_6$ alkenyl; $C_2$–$C_6$ alkynyl; $C_3$–$C_6$ cycloalkyl; $C_6$–$C_{10}$ aryl optionally substituted with halo, amino, $C_1$–$C6$ alkylamino, carboxy; $C_1$–$C_6$ alkoxy, and hydroxy; and heterocycloalkyl and heteroaryl having from 1 to 3 rings, each ring having from 0–3 hetero atoms selected from N, O, and S provided that at least one ring contains a heteroatom optionally substituted with halo, amino, $C_1$–$C_6$alkylamino, carboxy, $C_1$–$C_4$ alkoxy, and hydroxy;

$R_2$ and $R_3$ taken together may form $C_4$–$C_8$-alkylene or $C_4$–$C_8$-oxydialkylene in a pharmaceutically acceptable excipient or carrier.

2. The method of claim 1 wherein the compound is represented by structural formula I:
where:
X is halo;
Z is oxo (O═); and
Y is —$NHR_2$.

3. The method of claim 2
where:
X is Cl and is located in the 2(ortho) position of the phenyl dng;
$R_1$ is selected from hydrogen and methyl; and
$R_2$ is selected from, benzyl, methyl, 3-aminophenylmethyl, 3-amino-2-iodo phenylmethyl, 3-azido-2-iodophenylmethyl, biotinoyl, acetyl, phenylethyloxycarbonyl, malonoyl 3-(methylthio)propanoyl, 3-(methylsulfinyl)propanoyl, and 3-(methylsulfonyl)propanoyl.

4. The method of claim 1 wherein the compound is selected from the group consisting of:
5,6-dehydronorketamine;
N-acetyl- 5,6-dehyd ronorketamine;
6-acetylamino-6-(2-chlorophenyl)-2cyclohexen-1-one;
6-(2-chlorophenyl)-6-(1-phenylethyloxycarboxyamino )-2-cyclohexen-1-one;
6-(2-aminoacetyl)amino-6-(2-chlorophenyl)-2-cyclohexen-1-one;
6-(2-chlorophenyl)-6-(3-(methylthio )propanoyl)amino-2-cyclohexen-1-one:
6-(2-chlorophenyl)-6-hydroxy-2-cyclohexen-1-one;
6-biotinoylamino-6-(2-chlorophenyi)-2-cyclohexen-1-one;
6-(2-chlorophenyl)-6-(3-(aminophenyl)methyl)amino-2-cyclohexen-1-one;
6-(2-chlorophenyl)-6-methylamino-2-cyclohexen-1-one;
6-(2-chlorophenyl)-6-phenylmethlamino-2-cyclohexen-1-one;
6-(2-chlorophenyl)-6-(3-(methylsulfinyl)propanoyl)amino-2-cyclohexen-1-one; and
6-(2-chlorophenyl)-6-(3-(methylsulfonyl)propanoyl)amino-2-cyclohexen-1-one.

* * * * *